(12) United States Patent
Peters

(10) Patent No.: US 12,313,543 B2
(45) Date of Patent: May 27, 2025

(54) INDICATOR FOR SOIL MOISTURE CONTENT

(71) Applicant: PlantDoc LLC, Portland, OR (US)

(72) Inventor: Austin Peters, Portland, OR (US)

(73) Assignee: PlantDoc, LLC, Portland, OR (US)

( * ) Notice: Subject to any disclaimer, the term of this patent is extended or adjusted under 35 U.S.C. 154(b) by 317 days.

(21) Appl. No.: 17/658,974

(22) Filed: Apr. 12, 2022

(65) Prior Publication Data

US 2022/0349821 A1   Nov. 3, 2022

Related U.S. Application Data

(60) Provisional application No. 63/182,626, filed on Apr. 30, 2021.

(51) Int. Cl.
*G01N 21/95*    (2006.01)
*G01N 21/59*    (2006.01)
*G01N 33/24*    (2006.01)

(52) U.S. Cl.
CPC ............. *G01N 21/59* (2013.01); *G01N 33/24* (2013.01); *G01N 33/246* (2013.01)

(58) Field of Classification Search
CPC ....... G01N 21/59; G01N 33/24; G01N 33/246
See application file for complete search history.

(56) References Cited

U.S. PATENT DOCUMENTS

| | | | |
|---|---|---|---|
| 3,951,098 A * | 4/1976 | Meyers | G01N 21/29 73/73 |
| 8,997,682 B1 * | 4/2015 | Ashcroft | G01N 21/29 116/200 |
| 2016/0123867 A1 * | 5/2016 | Orihara | G01N 19/10 73/73 |

FOREIGN PATENT DOCUMENTS

JP    5692826 B2    4/2015

* cited by examiner

Primary Examiner — Jamil Ahmed
(74) Attorney, Agent, or Firm — Lee & Hayes, P.C.

(57) ABSTRACT

Devices are provided for indicating a moisture content of a substance such as soil. In an example, a device for indicating a moisture content of soil includes a stem configured to be inserted into the soil and an indicator coupled to the stem and configured to visually indicate the moisture content of the soil, the stem and the indicator each comprised of an absorbent material and at least the indicator including hydrochromic ink on the absorbent material.

20 Claims, 2 Drawing Sheets
(2 of 2 Drawing Sheet(s) Filed in Color)

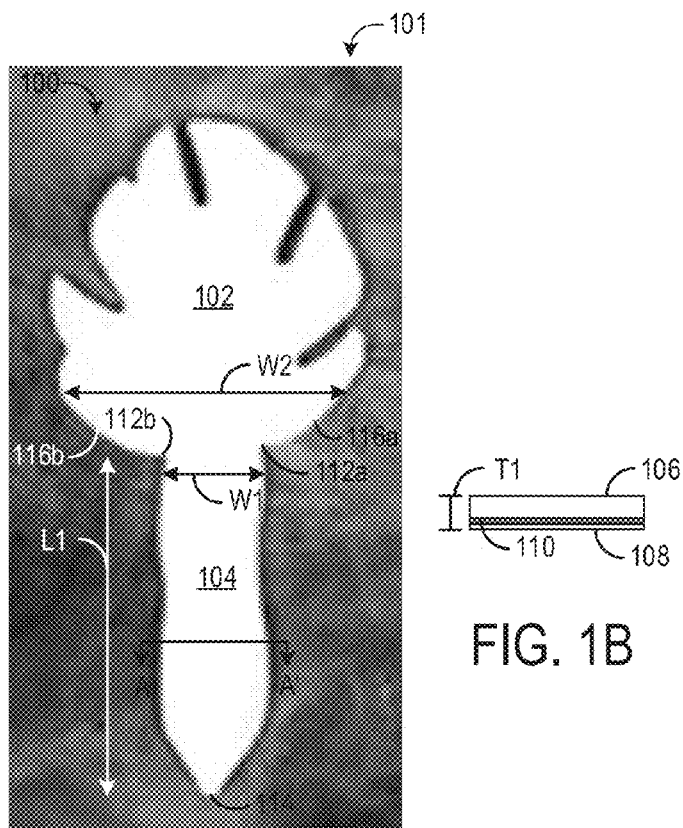
FIG. 1A
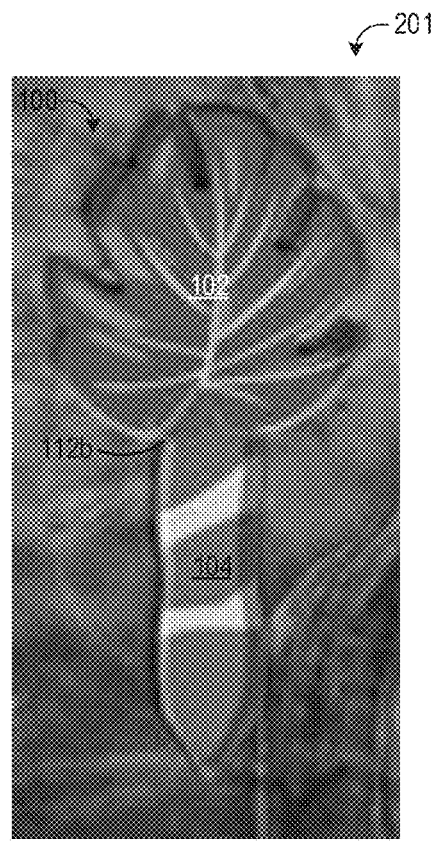
FIG. 1B
FIG. 2
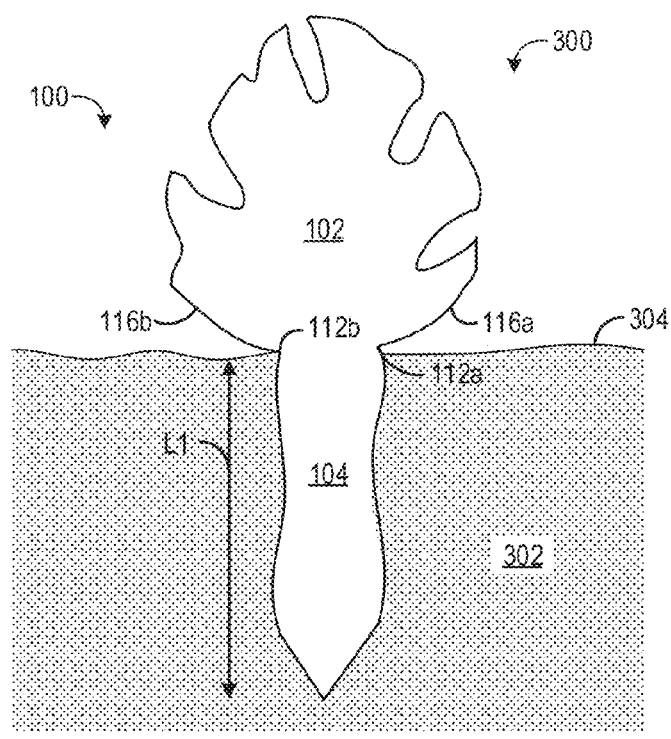
FIG. 3

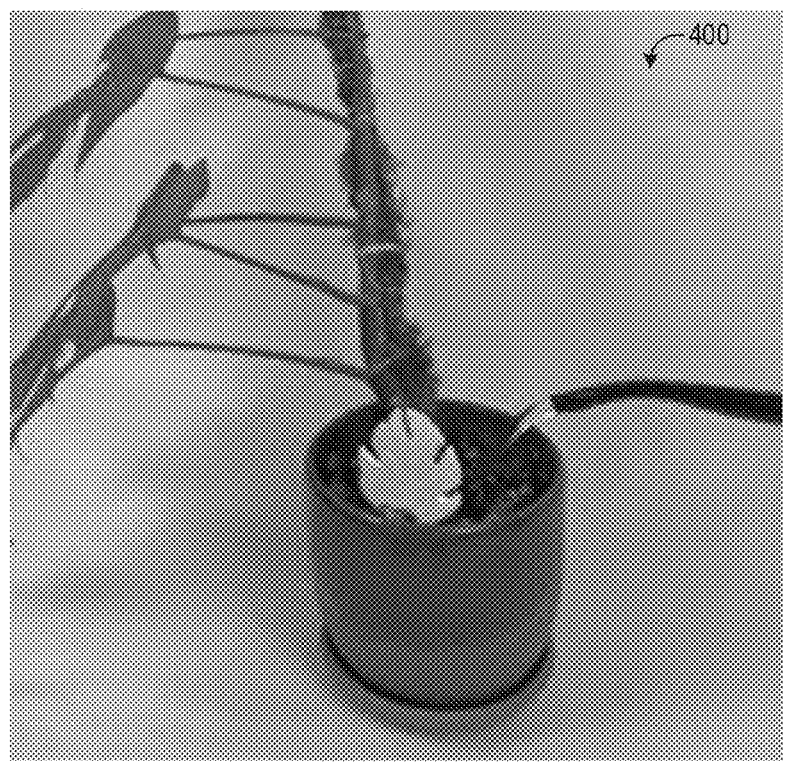
FIG. 4
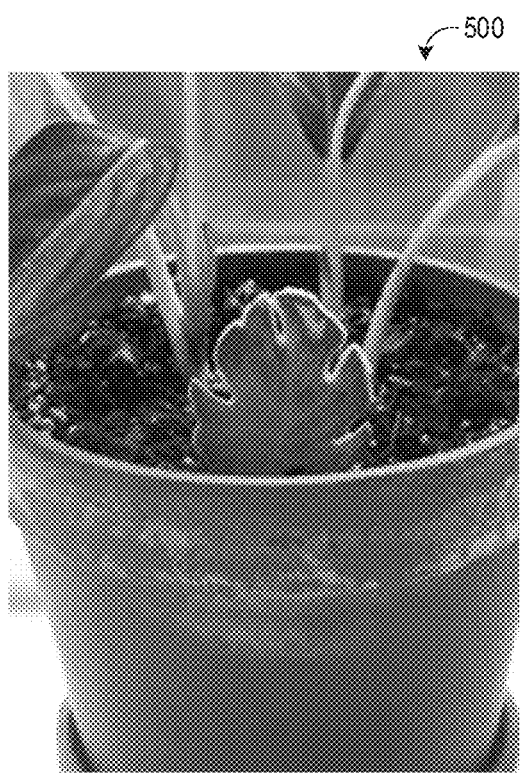 
FIG. 5          FIG. 6

INDICATOR FOR SOIL MOISTURE CONTENT

CROSS-REFERENCE TO RELATED APPLICATIONS

The present application claims priority to U.S. Provisional Patent Application No. 63/182,626, entitled "INDICATOR FOR SOIL MOISTURE CONTENT," and filed Apr. 30, 2021, the entire contents of which is hereby incorporated by reference for all purposes.

FIELD OF TECHNOLOGY

The present description relates generally to a moisture indicator, specifically a moisture indicator configured to detect a moisture level in soil.

BACKGROUND

Many plants, particularly indoor houseplants, demand consistent amounts of soil moisture to grow, thrive, and avoid fungal or bacterial contamination. Different plants may demand different moisture levels, and demanded moisture levels may fluctuate due to ambient conditions, geographical area/climate, and seasonality. Overwatering and underwatering can cause similar issues including wilting, browning edges, and yellowing leaves. Thus, it may be difficult to determine at a glance whether a plant needs more or less water. Without regularly checking the soil to a sufficient depth, many houseplants may suffer from under- or over-watering, impacting their appearance and decreasing their health and longevity. Currently available commercial moisture indicators tend to be expensive, prone to failure, and frequently only measure moisture levels at the very top layer of soil. Thus, a need exists for an inexpensive and reliable soil moisture indicator.

SUMMARY

Embodiments of a soil moisture indicator are provided herein. In one example, a device for indicating a moisture content of soil includes a stem configured to be inserted into the soil and an indicator coupled to the stem and configured to visually indicate the moisture content of the soil, the stem and the indicator each comprised of an absorbent material and at least the indicator including hydrochromic ink on the absorbent material.

To the accomplishment of the foregoing and related ends, certain illustrative aspects of the system are described herein in connection with the following description and the attached drawings. The features, functions, and advantages that have been discussed can be achieved independently in various embodiments of the present disclosure or may be combined in yet other embodiments, further details of which can be seen with reference to the following description and drawings. The summary is provided to introduce a selection of concepts in a simplified form that are further described below in the Detailed Description. This summary is not intended to identify key features or essential features of any subject matter described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows a device for measuring moisture content in soil in a first, dry state, according to an embodiment of the disclosure.

FIG. 1B schematically shows a cross-sectional view of the device of FIG. 1A.

FIG. 2 shows the testing device of FIG. 1A, in a second, wet state.

FIG. 3 schematically shows the device of FIG. 1A positioned in soil.

FIGS. 4-6 schematically show the device of FIG. 1A positioned in soil, in various states of dryness.

DETAILED DESCRIPTION

FIGS. 1A-6 show an example device 100 according to the disclosure. FIG. 1A shows a front view of the device 100 in a first state 101 where the device 100 is dry (e.g., holding less than a threshold amount of liquid). FIG. 1B shows a cross-sectional view of the device 100 taken across line A-A'. FIG. 2 shows a front view of the device 100 in a second state 201 where the device 100 is wet (e.g., holding more than the threshold amount of liquid).

Device 100 is configured for visually indicating a moisture content of soil or another substance (e.g., sand) via reversible hydrochromic ink. The hydrochromic ink may change in color/visual appearance when wet versus when dry. Thus, when the device 100 is placed in soil, the device 100 may absorb water in the soil and wick the water to the hydrochromic ink, causing the hydrochromic ink to change color as an indicator of the moisture level of the soil.

Device 100 includes an indicator 102 coupled to a stem 104. Each of indicator 102 and stem 104 may be comprised of an absorbent material 106, such as paper or wood pulp board. When the absorbent material is paper, the paper may be a multilayer composite paper. The absorbent material 106 may be configured to absorb and wick liquid such as water, and may have properties (e.g., thickness, material properties) that allow the liquid to be absorbed/wicked at a target rate while maintaining a structural integrity of the device (e.g., maintaining a shape, orientation, etc. of the device 100), as will be explained in more detail below. For example, the device 100 may have a thickness T1 (shown in FIG. 2) of 2-3 mm, which is comprised nearly completely of the absorbent material 106 (e.g., the thickness of the color change ink, described below, may be negligible), which may allow for desired absorption and wicking of liquid by the absorbent material. As shown in the Examples below, a 78 pt composite, multi-layer paper and an 80 pt wood pulpboard were each able to absorb and wick water at sufficient rates to be able to expose the hydrochromic ink to the water in soil, and thus may be used as the absorbent material, at least in some examples. In the example shown herein, the indicator 102 and the stem 104 are continuous (e.g., formed from the same piece of absorbent material). However, in other examples, the indicator 102 and the stem 104 are separate pieces that are coupled together.

Each of the indicator 102 and the stem 104 include one or more layers of color-change ink (referred to as hydrochromic ink 108) printed, painted, or otherwise applied to at least a front face of the absorbent material 106. The hydrochromic ink may be applied in one or more coats, for example, but not limited to, 2, 3, 4, 5, 6 or more coats, depending on a viscosity of the ink. In the example shown, the hydrochromic ink 108 may be opaque when dry, and herein has a white color when dry though other colors may also be used. The hydrochromic ink 108 may be applied such that, when dry, the hydrochromic ink obscures any underlying visual features of the absorbent material 106. The hydrochromic ink 108 be comprised of a pigment or other material that can absorb moisture, and when the pigment absorbs moisture, the refractive index of the pigment changes so that the pigment is opaque (e.g., white) when dry, and clear (e.g., translucent or transparent when wet). Thus, when the hydrochromic ink absorbs moisture, any markings or color on the underlying device become visible. Exemplary hydrochromic ink 108 may include one or more of diammonium zinc biscarbonate, sodium aluminum silicate, alumina trihydrate, and/or micronized amorphous silica gel. In some examples, the pigment may be included in an aqueous solution, an alcohol-based solution, in an emulsion (e.g., an acrylic acid ester copolymer emulsion), or another suitable formulation. The hydrochromic ink 108 may include other materials, such as photoinitiators. Further, the hydrochromic ink 108 may be non-toxic both to plants and micro-organisms. For example, in some aspects, the device may allow fungal or bacterial growth (e.g., to indicate fungal or bacterial growth in the soil and/or plant) due to the use of the device 100 in household settings. In other aspects, the device may be non-toxic to plants. Thus, the hydrochromic ink 108 may not include chromium, titanium, or other pigments that may be toxic, at least in some examples. Further still, while a hydrochromic ink 108 that is opaque white when dry and transparent or translucent when wet has been described herein, it is to be appreciated that other types of hydrochromic ink may be used, such as inks that are yellow when dry and blue when wet.

In some examples, an intervening layer 110 (or layers) of paint or ink may be present between the absorbent material 106 and the hydrochromic ink 108. In such examples, the intervening layer 110 may be of a different color (e.g., green) than the hydrochromic ink 108, but may be obscured by the hydrochromic ink 108 when the device 100 is in the first state 101. To ensure water absorbed and wicked by the absorbent material 106 is wicked to the hydrochromic ink 108, the intervening layer 110, when present, may be comprised of ink, paint, or another suitable material that allows water to be transmitted between the absorbent material 106 and the hydrochromic ink 108. In other examples, intervening layer 110 may be partial (e.g., present over some but not all of the absorbent material) or the intervening layer may be omitted and the hydrochromic ink 108 may be applied directly on the absorbent material 106. In examples, at least a portion of the absorbent material (e.g., a portion on which the hydrochromic ink is applied) has a color that is visible when the hydrochromic ink is transparent and is obscured when the hydrochromic ink is opaque. For example, FIGS. 2, 5 and 6 show that the absorbent material has a color or colors (e.g., green and white) when the hydrochromic ink is transparent and that the color(s) of the absorbent material are obscured when the hydrochromic ink is opaque. The color(s) of the absorbent material may be provided via the intervening layer as described above or as the color(s) of the absorbent material itself.

FIG. 2 shows the device 100 in the second state 201, where the device 100 has been exposed to water, allowing the absorbent material 106 to absorb water and wick the water along the width/length of the device 100 and to the hydrochromic ink 108. When the hydrochromic ink 108 is wet, the hydrochromic ink 108 becomes transparent, allowing the visual features of the absorbent material 106 and/or the intervening layer 110 to be seen. Thus, as shown by FIGS. 1A and 2, when the device 100 is exposed to water, the hydrochromic ink 108 turns from opaque (e.g., white) to transparent, and the visual appearance of the device 100 changes (e.g., to display the color/visual features of the absorbent material, herein a green color having features mimicking the visual appearance of a plant). It is to be appreciated that the term "dry," as used herein in reference to the device 100, may include the device 100 holding an amount of water (or other liquid) that is less than a threshold amount, where the threshold amount is an amount of water that causes the hydrochromic ink 108 to change color. The term "wet," as used herein in reference to the device 100, may include the device 100 holding an amount of water or other liquid that is equal to or greater than the threshold amount. Further, the device 100 may be fully dry (where the entirety of the device 100 holds less than the threshold amount of water needed to cause the ink to change color), fully wet (where the entirety of the device 100 holds the threshold amount or more of water needed to cause the ink to change color), or partially dry/partially wet (where some but not all of the device 100 holds less than the threshold amount of water needed to cause the ink to change color). In examples where the device 100 is partially dry, one or more regions of the device 100 (such as the stem) may be wet, while one or more other regions of the device 100 (such as the indicator or the top of the indicator) may be dry. In some aspects, additional layers of the same or a different ink may be applied over the hydrochromic ink. For example, a name, logo, or other information may be printed over the hydrochromic ink in such a way that the color change of the hydrochromic ink is still visible, but other information may also be conveyed.

The stem 104 and the indicator 102 may each have a size and shape configured to enable a user to place the device 100 in soil at a target depth that may be optimal for monitoring moisture content of soil in which a houseplant is planted, and to easily monitor the moisture content of the soil as the moisture content changes. For example, the stem 104 may have a length L1 that extends from a top region of the stem 104 (where the stem 104 transitions to/meets the indicator 102) to a bottom point 114 of the stem 104, where the stem terminates. The top region of the stem 104 may include a first top point 112a on a first (e.g., right) side of the stem and a second top point 112b on a second (e.g., left) side of the stem. The length L1 may be selected based on the optimal soil depth for monitoring the moisture content of the soil. In the example shown, the length L1 may be in a range of about 4-6 cm, such as 5 cm (e.g., 2 inches). Thus, when the device 100 is placed in soil such that the stem 104 is completely or nearly completely immersed in the soil, the stem 104 may absorb water in the top about 4-6 cm of the soil. In this way, the moisture content of the soil in the top about 4-6 cm of the soil may be monitored via the device 100, rather than the moisture content of only the very top layer of the soil, which may improve plant health as the top 4-6 cm of soil have been shown to be the most important for ensuring adequate moisture content to promote plant health. For example, the top layer may dry out before the soil 5 cm below the top layer, and if only the moisture content of the top layer is monitored, the plant may be overwatered. By monitoring the moisture content of the soil from the top layer to a suitable depth below the top layer (e.g., 5 cm), a more accurate assessment of the moisture level of the soil where the roots of the plant are located may be provided. In some examples, the device 100 may be sized to monitor the moisture content of soil in a relatively large pot (e.g., accommodating a relatively large plant) and thus the length L1 may be in a range of 8-12 cm, such as 10 cm (e.g., 4 inches), though other appropriate sizing may also be used. In some examples, the device 100 may have an overall length (from a top of the indicator 102 to a bottom of the stem 104) that is in a range from 20-35 cm (e.g., 8-12 inches), with the length L1 of the stem 104 being in a range of 10-16 cm (e.g., 4-6 inches).

The indicator 102 may be sized and shaped to provide a visual cue to a user to position the device 100 in the soil at the target depth. For example, the indicator 102 may have a first side edge 116a that extends from the first top point 112a of the stem 104 (e.g., where the stem 104 joins/transitions to the indicator 102) outward at an angle and/or with a curvature greater than zero. The indicator 102 may have a second side edge 116b that likewise extends from the second top point 112b at an angle and/or with a curvature, such that the width of the indicator is greater than a width of the stem at the region where the stem transitions to the indicator. For example, the side edges 116a, 116b may each curve outward and upward from the first and second top points 112a, 112b toward a top of the indicator 102. In another example, the indicator 102 may have a different shape, such as a rectangular or triangular shape, such that the side edges 116a, 116b extend outward at an angle relative to the extent of the stem 102, such as within a range of 45-90 degrees relative to a longitudinal axis of the stem 104. As shown, the stem 102 may have a first width W1 at or adjacent to (e.g., within 5 mm) the top region of the stem 104 (e.g., from the first top point 112a to the second top point 112b) and the indicator 102 may have a second width W2 adjacent to (e.g., within 1 cm) the top region of the stem 102, where the second width W2 is greater than the first width W1. The second width W2 may be twice as wide or three times as wide as the first width W1 (e.g., the first width W1 may be 1.5 cm and the second width W2 may be 4 cm). In this way, the shape and size of the indicator 102 relative to the stem 104 may visually prompt the user to position the device 100 in soil so that the stem 104 is fully immersed in the soil and the indicator 102 is positioned at and extends upward from the top of the soil. The indicator 102 may have a suitable length that is based on the length of the stem 104. For example, when the stem 104 has a length in the range of 4-6 cm, the indicator 102 may have a length in a range of 4-6 cm, and when the stem 104 has a length in the range of 8-12 cm, the indicator 104 may have a length in the range of 8-12 cm.

FIG. 3 schematically shows an example 300 of the device 100 positioned in soil 302. The soil 302 may have a top layer 304, where the soil terminates and is exposed to atmosphere. The soil 302 may have a suitable depth that is longer than 5 cm (e.g., 15-30 cm or another suitable depth). The device 100 may be positioned in the soil 302 so that the soil 302 surrounds the stem 104 and so that the indicator 102 is positioned above the top layer 304 of the soil 302. The increased width of the indicator 102 relative to the stem 104 may provide a cue to the user to insert the device 100 into the soil 302 until the bottom of the indicator 104 is at or near the top layer 304, which may ensure that the bottom point 114 of the stem 104 is positioned at the optimal soil depth.

When the device 100 is positioned in the soil 302, water in the soil 302 may be absorbed by the absorbent material 106 of the stem 102 and wicked upward to the absorbent material 106 of the indicator. When a sufficient amount of water has been wicked to the hydrochromic ink 108, the hydrochromic ink 108 transitions from opaque to clear, causing the color of the device 100 to change in correspondence to the amount of water in the soil 302. For example, when the soil 302 is relatively moist, the water may be absorbed and wicked relatively quickly, causing the color of the entire device 100 (e.g., both the stem 104 and the indicator 102) to change in a relatively short amount of time (e.g., less than 40 minutes). If the soil 302 is not relatively moist, water may be absorbed more slowly, and depending on the moisture content of the soil, the water may be maintained only in the stem 104 and the water may not be wicked (or fully wicked) to the indicator 102. In such examples, the stem 104 may still undergo a color change, which may be visualized when the device 100 is removed from the soil 302. In this way, the moisture content of the soil under the top layer 304 may still be assessed, which may prevent overwatering of the soil.

FIG. 4 shows an example 400 of the device 100 positioned in soil in a pot, with a plant in the soil. The device 100 shown in FIG. 4 is in the first, dry state, as the device 100 has just been positioned in the soil and/or because the soil has not been sufficiently watered. Once the soil is watered, the device 100 absorbs and wicks the moisture and thus changes color, as shown by example 500 of FIG. 5. As the soil dries out over time (e.g., in the week or month following the soil being watered), the water may start to evaporate from the device 100 and insufficient water may remain in the soil to keep the device 100 in the second, fully wet state. Under such conditions, the hydrochromic ink 108 may begin to return to the dry state, where the ink is opaque. In some examples, as shown by the example 600 of FIG. 6, the indicator 102 may begin to change color, starting at the top and slowly moving downward (e.g., such that the top of the device is white where the color of the absorbent material is obscured by the opaque hydrochromic ink and the remainder of the device is green where the color of the absorbent material is visible due to the transparent hydrochromic ink). Eventually, if the soil is very dry, the entire device 100 may return to the dry state.

The device 100 may provide advantages over traditional moisture indicators. As explained above, the shape and/or size of the stem and indicator are specifically configured so that the device is placed about 5 cm (e.g., 2 inches) into soil, meaning the device measures the moisture in the top 5 cm or so of soil, the most important for houseplant health. While any suitable absorbent material may be used in manufacturing the device, in some aspects an absorbent material may absorb at least 1.5 mL/g of water in a set period of time. In some aspects, the absorbent material may absorb at least 2.0 mL/g of water in the set period of time. In further examples, the absorbent material may absorb no more than 50 g/m$^2$ (Cobb value) in the set period of time. In some embodiments, the absorbent material may absorb no more than 26 g/m$^2$ (Cobb value according to ISO 535) in the set period of time. The set period of time may be in a range of 10-20 minutes, such as 15 minutes. For example, the device may be made of organic materials including but not limited to paper, cardboard, cotton, cellulose, or wood pulp board, each of which are compostable/biodegradable. Thus, the device may have minimal environmental impact. Additionally, the absorbent organic material may allow growth of bacteria, fungus, etc., which may allow the device to provide an indication if such potential pathogens are also present in the soil and/or on any plants present in the soil. In some aspects, the absorbent material may be selected to have specific wicking properties. For example, in some aspects the absorbent material may be capable of wicking water at least 2.5 inches above the water surface within a given amount of time. In further examples, the absorbent material may wick water to a suitable height within the set period of time (e.g., 20 minutes) when the soil is sufficiently moist. For example, in some aspects, the absorbent material may wick water at least to a height of 10 cm (as measured from a bottom of the stem), at least to a height of 15 cm, at least to a height of 20 cm, or more. In some aspects, the absorbent material may be selected based on the overall length of the device, such that a first absorbent material may be selected for shorter devices (e.g., with an overall length of 4-8 inches) and a second, different absorbent material may be selected for longer devices (e.g., with an overall length of 8-12 inches). In such examples, the absorbent material may be selected in order to provide wicking to a desired height. In some aspects, the absorbent material may be selected to have specific durability. For example, the absorbent material may have sufficient rigidity so that it does not bend when saturated with water.

Further, because the full surface of the indicator is visible above the soil and not obscured (e.g., as in some conventional moisture indicators), the device allows for much clearer communication of the soil moisture level as well as the trajectory of whether the soil is beginning to dry out or is maintaining a certain moisture level. Especially during seasonal changes, soil that normally dries out in a week can stay moist for a month and vice versa. The indicator of the device more clearly communicates this because of its proximity to the soil, depth in the soil, and highly visible image display. Further still, the device reflects watering patterns, as "high water marks" become visible if the soil is watered before it fully dries out, providing helpful information for plant owners to adjust their habits if needed.

Additionally, the device communicates better than traditional indicators because it is fully visible, has a wide and visible indicator, and directly touches and inserts into the soil. This communicates optimal watering time better because the return of opacity can be observed all the way into the soil insertion point (e.g., on the stem). For example, a small area of color at the soil insertion point may indicate that the top 5 cm of soil is still moist, and therefore the plant may not need to be watered yet (true of most house plants).

While the device is shown herein as including a green indicator in the shape of a *Monstera* leaf, other indicator shapes and colors are possible without departing from the scope of this disclosure, such as other plants, pets (e.g., cats, dogs), or virtually any other shape, size, or color. However, to clearly communicate the moisture level and assist in placing the stem at the proper depth for monitoring soil moisture content, the indicator may be wider than the stem or otherwise visually communicate which part of the device is configured to be inserted in the soil and which part of the device is configured to be positioned above the soil. For example, the indicator may be the same width as the stem, narrower than the stem, or wider than the stem, and in some examples the device may include colors or marks to visually indicate a preferred depth of the device that should be inserted into the soil. In some examples, the device may be circular or another suitable shape (e.g., rectangular).

Hereinafter, the present invention will be described in detail with reference to examples. It is to be understood that the terminology employed herein is used for the purpose of describing particular embodiments only and not to limit the scope of the invention.

EXAMPLES

Example 1

Material Absorbency Test

A test was conducted to determine which absorbent material candidates had sufficient absorbency to be used in a moisture indicating device as described herein. Four candidate materials were tested: a multilayer composite paper material having a thickness of 78 pt (from Custom-Comet, Portland, OR), a wood pulp board having a thickness of 80 pt (from Royer Corporation, Madison, IN), recycled paper of a single material having a thickness of 40 pt (CustomComet), and chipboard with an adhesive printed surface (Ad Magic Print & Play, Vancouver, WA). Each absorbent material candidate was placed into a container of water having a known volume. After 15 minutes, which was a sufficient amount of time to ensure the water had been absorbed, each candidate material was removed and the remaining volume of water was measured. A candidate material was deemed sufficiently absorbent if the material absorbed more than 2.0 mL/g of water.

Two of the candidate materials absorbed more than 2.0 mL/g of water: the composite paper (which absorbed 2.14 mL/g) and the wood pulp board (which absorbed 2.19 mL/g). The recycled paper absorbed 1.49 mL/g and the chipboard absorbed 0.26 mL/g. Thus, the composite paper and the wood pulp board were determined to have sufficient absorbency.

Example 2

Surface Absorbency Rate Test

A test was conducted to determine the surface absorbency rate of the four absorbent material candidates of Example 1. Each absorbent material candidate was positioned on a flat surface and 1 mL of water was dispensed on the top surface of the candidate material. The amount of time it took for the water to be absorbed in the material was measured. A candidate material was deemed to have a relatively fast absorbency rate if the material absorbed the water in less than 20 minutes.

Three of the candidate materials absorbed the 1 mL water in less than 20 minutes: the composite paper (which absorbed the water in 12:00 minutes), the recycled paper (which absorbed the water in 2:05 minutes), and the wood pulp board (which absorbed the water in 5:00 minutes). Thus, the composite paper, the recycled paper, and the wood pulp board were determined to have a sufficient surface absorbency rate.

Example 3

End Absorbency Rate Test

A test was conducted to determine the absorbency rate of the four absorbent material candidates of Example 1 when each candidate material was placed on end (e.g., vertically upright). Each absorbent material candidate was positioned vertically upright in 1 mL of water. The amount of time it took for the water to be absorbed in the material was measured. A candidate material was deemed to have a relatively fast absorbency rate if the material absorbed the water in less than 20 minutes.

Three of the candidate materials absorbed the 1 mL water in less than 20 minutes: the composite paper (which absorbed the water in 1:00 minute), the recycled paper (which absorbed the water in 5:10 minutes), and the wood pulp board (which absorbed the water in 1:00 minute). Thus, the composite paper, the recycled paper, and the wood pulp board were determined to have a sufficient end absorbency rate.

Example 4

Material Absorbency Height Test

A test was conducted to determine the height of water absorption of the four absorbent material candidates of Example 1. Each absorbent material candidate was positioned upright in 0.5 inches of water. The height of the water absorption by each material was measured at intervals over a period of 40 minutes. A candidate material was deemed to have a sufficient ability to wick water if the water was absorbed at least 3 inches above the water surface in less than 40 minutes. The results are show below in Table 1.

TABLE 1

| Absorbent material | Absorption height (inches) | Time |
|---|---|---|
| Composite paper | 0.5 | 0:45 |
|  | 1.0 | 4:20 |
|  | 1.5 | 8:00 |
|  | 2.0 | 13:45 |
|  | 2.5 | 20:00 |
|  | 3.0 | 25:00 |
|  | 3.5 | 28:00 |
| Wood pulp board | 0.5 | 1:15 |
|  | 1.0 | 2:15 |
|  | 1.5 | 4:15 |
|  | 2.0 | 9:05 |
|  | 2.5 | 12:40 |
|  | 3.0 | 16:00 |
| Recycled paper | 0.5 | 2:03 |
|  | 1.0 | 9:10 |
|  | 1.5 | >40:00 |
| Chipboard | 0.5 | >40:00 |

Two of the candidate materials were able to wick the water to a height of 3 inches or greater in less than 40 minutes: the composite paper and the wood pulp board. Thus, the composite paper and the wood pulp board were determined to have sufficient water wicking properties.

Example 5

Material Durability Test

A test was conducted to determine the ability of the four absorbent material candidates of Example 1 to maintain a rigid upright structure when soaked with water. Additional material candidates were also evaluated, a 55 pt wood pulpboard, a 35 pt wood pulpboard, a 24 pt paperboard, and an 18 pt paperboard. Each absorbent material candidate was positioned vertically upright and fully wet with water. A candidate material was deemed to be successfully rigid if the material did not bend once saturated with water.

All four of the candidate materials from Example 1 where able to maintain sufficient rigidity when saturated with water, along with the 55 pt and 35 pt wood pulpboards. Neither of the paperboard candidate materials were able to maintain rigidity when saturated with water.

Example 6

Ink Viscosity

The viscosity and density of a candidate hydrochromic ink material was measured. The candidate hydrochromic ink is a sprayable hydrochromic ink from SFXC (Newhaven, East Sussex, UK) with a stock density of 1.13 g/mL. The viscosity of the candidate ink was measured by placing 100 mL of the ink in a cup with a 2 mm opening and measuring the amount of time for the ink to drain from the cup, at a temperature of 68 degrees F. The ink took 2:15 to drain from the cup. At this viscosity and density, the ink could not be sprayed onto an absorbent material. Thus, the ink was diluted to a density of 1.1 g/mL (e.g., 3 parts ink to 1 part water). The ink at this dilution was applied to the absorbent material in two coats to ensure the absorbent material was obscured by the ink.

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

As used herein, the term "about" means a range of values including the specified value, which a person of ordinary skill in the art would consider reasonably similar to the specified value. In embodiments, about means within a standard deviation using measurements generally acceptable in the art. In some aspects, about means±10%.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A biodegradable device for indicating a moisture content of soil, comprising:
a stem configured to be inserted into the soil; and
an indicator coupled to the stem and configured to visually indicate the moisture content of the soil, the stem and the indicator each comprised of an absorbent material and at least the indicator including hydrochromic ink on the absorbent material;
wherein the indicator is configured to display a pattern of high water marks on a surface of the indicator as water evaporates.

2. The biodegradable device of claim 1, wherein the indicator is configured to be positioned above the soil, wherein the stem has a first width at a top region of the stem where the stem couples to the indicator and the indicator has a second width at a bottom region where the indicator couples to the stem, and wherein the second width is larger than the first width.

3. The biodegradable device of claim 1, wherein the stem has a length of at least two inches.

4. The biodegradable device of claim 1, wherein both the stem and the indicator include the hydrochromic ink on the absorbent material.

5. The biodegradable device of claim 1, wherein the stem and/or the indicator include non-hydrochromic ink on the absorbent material and the hydrochromic ink is present on the non-hydrochromic ink.

6. The biodegradable device of claim 1, wherein the hydrochromic ink is configured to change from being opaque to being transparent when the hydrochromic ink is exposed to water in the soil and/or in the absorbent material.

7. The biodegradable device of claim 6, wherein the absorbent material comprises paper and/or cardboard.

8. The biodegradable device of claim 7, wherein the paper comprises a multilayer composite paper.

9. The biodegradable device of claim 6, wherein the absorbent material comprises a wood pulp board.

10. The biodegradable device of claim 6, wherein the absorbent material is configured to maintain a same shape, size, and structure when wet as when dry.

11. The biodegradable device of claim 6, wherein the hydrochromic ink is a reversible hydrochromic ink such that the hydrochromic ink, after becoming transparent when exposed to the water, is configured to change from being transparent to being opaque when the hydrochromic ink is no longer exposed to water in the soil and/or in the absorbent material.

12. The biodegradable device of claim 1, wherein the hydrochromic ink comprises a white pigment and an acrylic acid ester copolymer emulsion.

13. The biodegradable device of claim 1, wherein the absorbent material is configured to support growth of one or more organisms in order to provide an indication of a presence of the one or more organisms in the soil.

14. A method, comprising:
wicking water in soil via capillary action by a stem of a device positioned in the soil to an indicator coupled to the stem and positioned above the soil, wherein the indicator and the stem are made of a same absorbent material; and
visually indicating a moisture content of the soil via the indicator, where the indicator is configured to change color when exposed to water,
wherein high water marks become visible by creating watering patterns on a surface of the indicator as the water evaporates.

15. The method of claim 14, wherein at least the indicator includes a hydrochromic ink on the absorbent material of the indicator.

16. The method of claim 15, wherein wicking water in the soil by the stem to the indicator comprises wicking the water with the absorbent material of the stem to the absorbent material of the indicator, and wherein visually indicating the moisture content of the soil via the indicator comprises exposing the hydrochromic ink on the absorbent material of the indicator to the water, wherein the water is wicked to the hydrochromic ink by the absorbent material of the stem and the indicator.

17. The method of claim 16, wherein visually indicating the moisture content of the soil via the indicator comprises:
indicating that the moisture content is sufficient when the hydrochromic ink changes from opaque to transparent; and
indicating that the moisture content is insufficient when the hydrochromic ink changes from transparent to opaque.

18. The method of claim 14, wherein wicking water in soil via capillary action by the stem to the indicator comprises wicking water in the soil present two inches below a top of the soil.

19. A device for indicating a moisture content of soil, comprising:
a stem configured to be inserted into the soil, the stem having a first width at a top region of the stem; and
an indicator coupled to the stem at the top region of the stem and having a second width at a bottom region of the indicator where the indicator couples to the stem, the second width larger than the first width, the indicator configured to be positioned above the soil and to visually indicate the moisture content of the soil, the stem and the indicator each comprised of an absorbent material and at least the indicator including reversible hydrochromic ink on the absorbent material, the absorbent material configured to absorb at least 1.5 mL/g of water in a set period of time,
where the reversible hydrochromic ink is configured to change from being opaque to being transparent when the reversible hydrochromic ink is exposed to water in the soil and/or in the absorbent material and the reversible hydrochromic ink, after becoming transparent when exposed to the water, is configured to change from being transparent to being opaque when the reversible hydrochromic ink is no longer exposed to water in the soil and/or in the absorbent material,
wherein the indicator is configured to display high water marks by creating a watering pattern on a surface of the indicator as the water evaporates; and
wherein the device is made of organic materials.

20. The device of claim 19, wherein at least a portion of the absorbent material has a color that is visible when the reversible hydrochromic ink is transparent and is obscured when the reversible hydrochromic ink is opaque.

* * * * *